United States Patent [19]
Cluzeau et al.

[11] Patent Number: 6,141,985
[45] Date of Patent: Nov. 7, 2000

[54] SELF-CONTAINED AND PORTABLE CRYOGENIC APPARATUS USING CARBON DIOXIDE IN LIQUID/SOLID PHASES

[75] Inventors: Christian Cluzeau, Salins les Bains; Jacky Desbrosse, Huiron, both of France

[73] Assignees: Societe Cryonic Medical, Salins les Bains; Societe Vallourec Composants Automobiles Vitry, Vitry le Francois, both of France

[21] Appl. No.: 09/263,829

[22] Filed: Mar. 8, 1999

[30] Foreign Application Priority Data

Mar. 6, 1998 [FR] France .................. 98 02757

[51] Int. Cl.[7] .............. F25D 3/00; F25D 3/12; F17C 9/02; A61B 18/18
[52] U.S. Cl. .............. 62/293; 62/384; 62/50.2; 606/22
[58] Field of Search ............ 62/293, 294, 384, 62/50.2; 606/20, 22, 25, 26

[56] References Cited

U.S. PATENT DOCUMENTS

| | | | |
|---|---|---|---|
| 2,258,863 | 10/1941 | Reynolds | 62/293 |
| 3,259,131 | 7/1966 | Kanbar et al. | 606/25 |
| 3,993,250 | 11/1976 | Shure | 239/332 |
| 4,280,499 | 7/1981 | Sguazzi | 62/50.2 |
| 5,289,689 | 3/1994 | Cornwell et al. | 62/64 |

FOREIGN PATENT DOCUMENTS 0 633 008  1/1995  European Pat. Off. .

*Primary Examiner*—William Doerrler
*Attorney, Agent, or Firm*—Young & Thompson

[57] ABSTRACT

A self-contained portable cryogenic apparatus that operates at the temperature (of the order of −78° C. at atmospheric pressure) reached by reducing the pressure of carbon dioxide ($CO_2$) or equivalent in liquid/solid phase, comprising a reservoir of pressurized liquefied $CO_2$, the drawing off head being connected to a liquid/solid $CO_2$ pressure reduction and ejection system, and comprising a control device, a pressure reduction device and a device for checking the temperature in the area to which it is applied, remarkable in that the top of the $CO_2$ reservoir is arranged on the apparatus such that during the entire usage period, only the liquid part of the $CO_2$ inside the reservoir comes into contact with the head so that it is drawn off and forced towards the application area through a pressure reduction and ejection system. The apparatus is particularly suitable for use in sports medicine in the form of a spray gun.

17 Claims, 3 Drawing Sheets

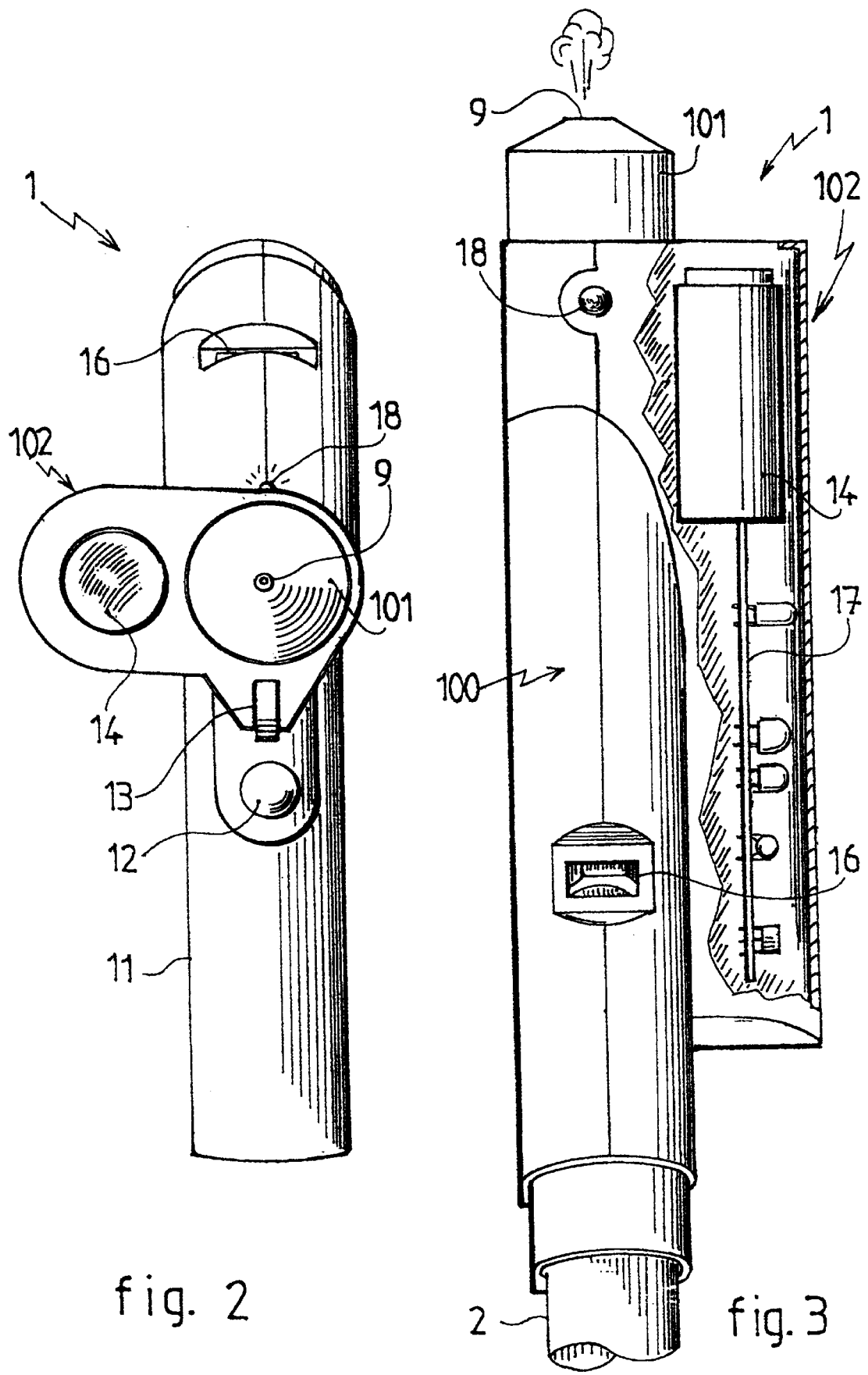

6,141,985

SELF-CONTAINED AND PORTABLE CRYOGENIC APPARATUS USING CARBON DIOXIDE IN LIQUID/SOLID PHASES

FIELD OF THE INVENTION

The invention relates to a self-contained and portable cryogenic apparatus particularly suitable for cryotherapy which is defined as therapy through the use of cold, which is very efficient in the treatment of a number of complaints that can be grouped into four main categories:

pain reduction; it is known that information transmitted through body sensory organs is considerably slowed down by cold, to the extent that electrical flows generated by nociceptors in the nerve fibers is itself considerably slowed, thereby attenuating pain, treatment of inflammations; it is known that a traumatism or a rheumatism produces inflammatory enzymes and that this production is strongly reduced by a cryotherapic treatment, stimulation of circulation; it is also known that cold introduces a vasomotor reflex and intensifies drainage action, muscular relaxation; finally, it is known that cold can produce an in-depth reflex response by reducing muscle tonicity; note that cold is much more efficient than heat in this respect, provided that treatment consists of applying intense cold which must also induce a very fast temperature drop. In the past, cooling sources used in cryotherapy apparatuses were either refrigerated air, or more frequently liquid nitrogen, and these sources are subject to many constraints which usually limit the mobility of the treatment apparatus. Small low pressure gas spray cans are used almost exclusively for applications related to sport, which is one of the major applications of cryotherapy, which are capable of reducing the temperature relatively slowly down to not less than −18° C. in the area of a local traumatism.

BACKGROUND OF THE INVENTION

This is why European patent EP-0.633.008 submitted by the applicant proposes to use compressed carbon dioxide ($CO_2$) as a source of cooling for cryotherapy, the intrinsic characteristic of carbon dioxide being that it can reduce the temperature down to −78° C. at atmospheric pressure. According to the information provided in this patent, the use of carbon dioxide in the form of a liquid/vapor mix can keep the pressure in the receptacle constant while it is being emptied; this pressure is simply the saturating vapor pressure which depends directly on the temperature of the receptacle. Thus, carbon dioxide occurs in two phases (namely solid and gas) when the pressure is reduced to atmospheric pressure. The solid phase, also called dry ice, extracts the maximum amount of heat from the skin of the patient to be treated. When it comes into contact with the skin, dry ice sublimates and thus absorbs a large quantity of heat. It is therefore essential to extract carbon dioxide from the receptacle in the liquid phase in order to produce intense cold and an extremely fast temperature drop at the same time.

In order to achieve this result, the apparatus according to the previous patent includes a plunger tube inside a pressurized liquid carbon dioxide cylinder, this plunger tube starting from the top of the cylinder and extending over its entire length. Thus, the liquid phase of $CO_2$ is drawn off and is then sprayed into a flexible pipe by means of a pressure reduction and ejection system fitted with a control handle and a diffuser which adjusts the shape, dimension and temperature of the $CO_2$ jet on the area to be treated.

This apparatus is heavy, and is used mainly by professionals such as physiotherapists. It is completely unsuitable for any environment other than conventional traumatology departments, for example such as sport grounds, racing courses or stud farms.

SUMMARY OF THE INVENTION

Therefore, in order to overcome these disadvantages, the invention proposes a self-contained, lightweight and portable apparatus capable of producing intense cold resulting in a very fast temperature drop, while providing maximum thermal safety conditions. It is easy to understand that spraying dry ice onto a patient's skin must be very carefully controlled, to the extent that the skin surface temperature must never drop below 0° C., otherwise organic tissues would be damaged. Therefore, in order to make the apparatus according to the invention completely self-contained, it is vital that the temperature of the area thus treated should be measured without any contact with the patient but in direct relation with the portable apparatus in order to avoid any manipulations that would considerably slow down the operation. Consequently, the invention proposes a portable cryogenic apparatus that operates at the temperature (of the order of −78° C. at atmospheric pressure) reached after reducing the pressure of carbon dioxide ($CO_2$) or equivalent in liquid/solid phase, comprising a reservoir of pressurized liquefied $CO_2$, the top of the reservoir being connected to a liquid/solid $CO_2$ pressure reduction and ejection system, and comprising a control device, a pressure reduction device and a means of checking the temperature in the area to which it is applied, which is remarkable in that the top of the $CO_2$ reservoir is arranged on the apparatus such that during the entire usage period, only the liquid part of the $CO_2$ inside the reservoir comes into contact with the top of the cylinder so that it is drawn off and forced towards the application area through a pressure reduction and ejection system.

In this sense, the apparatus according to the invention is characterized in that the reservoir, which is beneficially in the general shape of a conventional compressed gas cartridge fitted with a special drawing off head at its end comprising means of attachment to and detachment from the apparatus and devices for setting up a communication towards its pressure reduction and ejection system, is located above the apparatus when it is in the operating position, the cartridge being inclined in the vertical plane and the drawing off head facing downwards towards the apparatus to which it is fixed.

According to another essential characteristic of the apparatus according to the invention, it is designed to be equipped with a temperature measurement system in order to inform the operator when the surface temperature of the area being treated has reached a critical limit, for example in cryotherapy when the skin temperature approaches 0° C. The most interesting existing techniques for temperature measurements in cryotherapy can be grouped into three categories, namely resistive probes, heat sensitive self-sticking pads, and remote pyrometers (particularly infrared pyrometers). Infrared pyrometers operate based on the principle that the radiation emitted by any body is proportional to the fourth power of its temperature, and are suitable for the self-contained and portable nature of the apparatus according to the invention; furthermore, infrared pyrometers are quite capable of making extremely fast measurements at a precise distance from the treatment area, provided that there is an electricity power supply and that the pyrometer focal distance is suitably chosen; it is known that if the treatment distance is too short (for example of the order of 3 to 4 centimeters) the temperature gradient in the skin subjected to the cryotherapy treatment is so high that the temperature of the treated area and the temperature of the area measured by the pyrometer are very different, so that it is impossible to issue a sound or visible alarm, so that there is a danger for the patient being treated. Thus, and according to another important characteristic of the invention, it is proposed to place an approach guide between the apparatus and the area being treated so that the pyrometer can be accurately and reliably placed at the required focal distance; according to one preferred embodiment, the approach guide will consist of a simple sliding rod that controls the distance between the pyrometer and the area to be treated; this rod may also contribute to the safety of the apparatus; for example, it will be impossible to switch the apparatus on unless this rod is in the external measurement position, as explained below; this prevents accidental use, particularly by children.

According to another characteristic of infrared pyrometers, an expert in the subject will find it easy to calculate the focal distance of the pyrometer such that the measurement spot on the part to be treated is always outside the area in which dry ice is sprayed, such that the measurement is made on a treated area and the recorded temperature is not the temperature of the dry ice, which would be the case if the measurement spot was within the area in which $CO_2$ sublimates.

BRIEF DESCRIPTION OF THE DRAWINGS

Other characteristics and advantages will become even clearer from the description of a self-contained and portable cryogenic apparatus given as a preferred example but which is in no way limitative, with reference to the drawings in which:

FIG. 2 shows the front view corresponding to the previous figure, FIG. 3 shows the top view corresponding to FIG. 1, and shows the arrangement of the pyrometer and its control electronics in a partially exposed view.

DETAILED DESCRIPTION OF THE INVENTION

Figure 1:
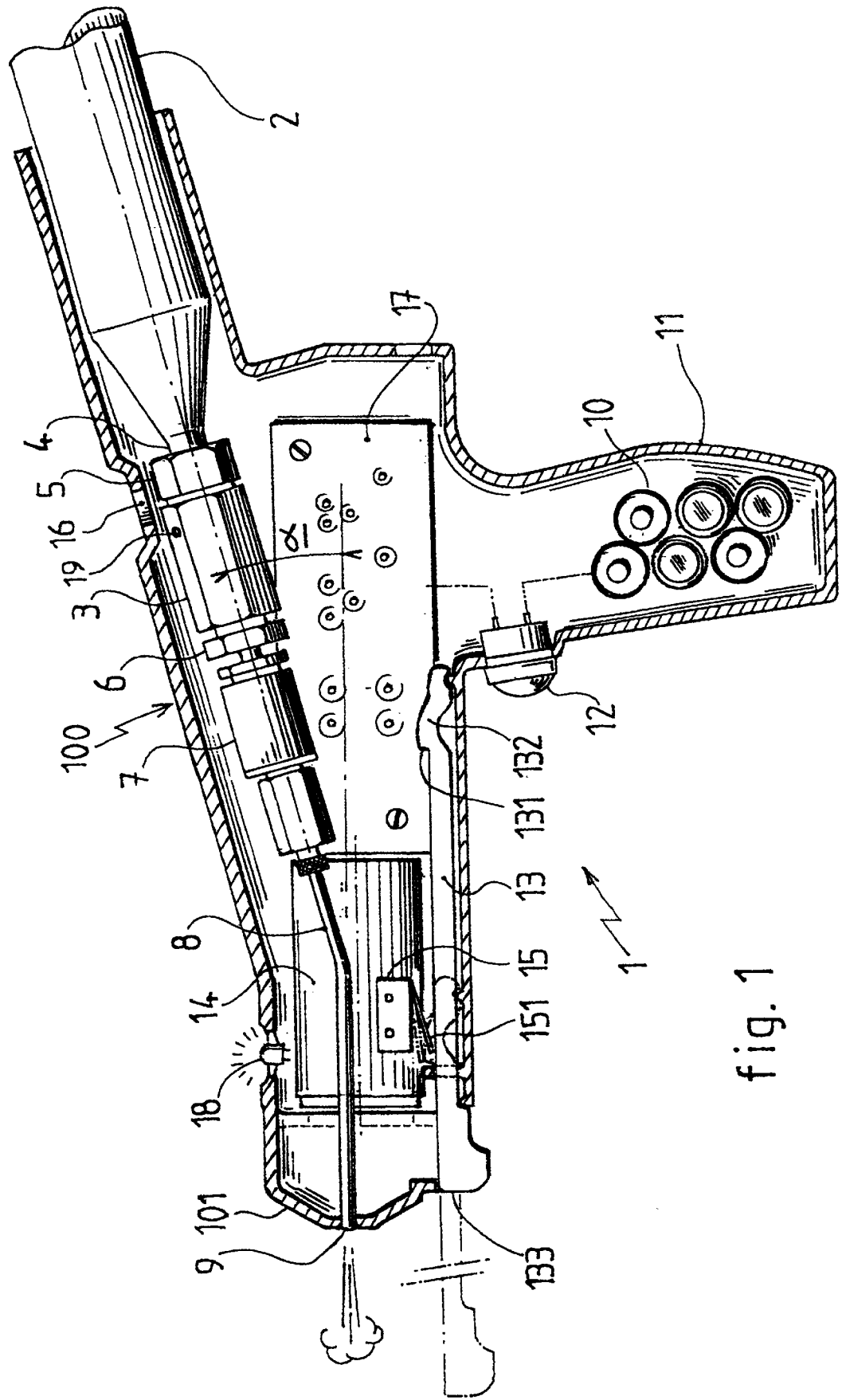
FIG. 1 shows an elevation of the apparatus and a vertical section diagrammatically showing the general shape of the portable apparatus and the relative arrangement of its main components.

The cryogenic apparatus 1 according to the figures that will be described below is designed particularly for cryotherapy for man or animals.

According to FIG. 1, the general shape of the apparatus 1 is a spray gun made in a plastic housing arranged on the inside to contain the functional devices of apparatus 1; this apparatus is supplied by a cartridge 2 of $CO_2$ in the liquid phase, inserted at the back at a inclination from the vertical that will be described later. The body 100 of the spray gun on which the cryogenic spray gun pressure reduction system is fitted comprises a support 3 at the back that holds the drawing off head 4 of the cartridge 2 through a connection part 5 on one side, and on the other side a filter 6 which will be described in more detail later, an in-line solenoid valve 7 that opens up a communication between the carbon dioxide $CO_2$ and a cranked pressure reduction and ejection tube 8 to open up at the front end 9 of the approximately horizontal barrel and to spray the $CO_2$ in the liquid/solid phase towards the area to be treated (not shown in the figures).

Solenoid valve 7 operating in "On-Off" mode is a frequently known type, for example like that available in the catalog of the Swiss "Fluid Automation Systems" company. It is energized at 12 volts DC by a set of batteries 10 arranged conventionally inside the handle 11 used to hold spray gun 1, using a stack of elements giving maximum electrical operating safety. Naturally, the user holding spray gun 1 must press in a switch 12 fitted on the front of handle 11, in the same way as a conventional trigger, using his index finger in order to activate solenoid valve 7 and consequently release $CO_2$ in liquid/solid form at the spray gun outlet point 9.

A rod 13 aligned under the barrel 101 of spray gun 1 acts as an approach guide and may slide horizontally from a rest position (shown in continuous lines in FIG. 1) inside barrel 101, to a working position (the rear part of this position inside the spray gun is shown in thin chained dotted lines in FIG. 1) corresponding to the appropriate distance for optimum spraying of dry ice onto the area to be treated, and also for accurate and precise checking of the temperature of the area by means of an infrared pyrometer 14 (shown in FIGS. 2 and 3), as will be described later.

Accessorily, a blade switch 15 is provided inside the barrel of spray gun 1 and will be normally open whenever rod 13 is not pulled out to its full extent, in other words in the working position for the spray gun; as soon as rod 13 is pulled all the way out, switch 15 is in the closed position due to a bossing 132 fitted on the inside end of rod 13, thus energizing the infrared pyrometer and secondly enabling the solenoid valve 7 to close by acting on the control switch 12.

The cryogenic spray gun 1 thus formed is suitable particularly for cryotherapy applications on man or animals, and is particularly useful for emergencies at sports events in order to treat pain, contusions, sprains, edemas, bruises, torn muscles, cramp, contractures, shoulder—collar bone dislocations, and for acute care in the treatment of reactive inflammations, tendinitis, bursitis and also tenosynovitis, periostitis, etc.

In all these cases in which the self-contained and portable apparatus according to the invention is used, all that is necessary is to insert a cartridge of liquefied pressurized $CO_2$ prepared in accordance with standards and specifications for medical use, onto the back of spray gun 1, making sure that the cartridge is well positioned on its support 3 by looking through display window 16 placed for example on the top part of spray gun 1. The operator then extends rod 13 which acts as an approach guide pulling it outwards along the line of the spray gun as far as a stop 131, thus forming a device which is practical for holding the apparatus at the right distance from the area to be treated; furthermore, the stop 131 forms a bossing 132 capable of pushing a strip 151 controlling the main switch 15 backwards to switch on the electronics 17 (FIG. 3) that controls the main functions of the apparatus 1. The user picks up the apparatus using its ergonomic handle 11, and usually holds it such that the barrel 101 of the spray gun 1 is approximately horizontal, which has the automatic effect of holding the cartridge 2 with the head downwards at all times at a vertical inclination α of at least 15° from the horizontal plane such that when being used, all that comes out of the cartridge 2 is $CO_2$ in the liquid phase, and never in the vapor phase. During use, simply tilt the barrel of the spray gun 1 downwards towards the painful area or the inflammation to be treated (which beneficially further increases the inclination α of the cartridge), holding the outlet end 9 of the pressure reduction and ejection tube 8 at a distance such that the distal end 133 of the rod 13 is practically in contact with the area to be treated. The operator then presses switch 12 like a trigger to activate solenoid valve 7 and draw liquid $CO_2$ off from cartridge 2 to take it through the pressure reduction tube 8 towards the end 9 and to spray it onto the treatment area in the form of dry ice, by means of continuous and crosswise forward and backward movements above the area to be treated; the dry ice on the patient's skin then sublimates and causes a very fast temperature drop by removing calories during the sublimation operation, as described above. When the infrared pyrometer 14, operating as described later, detects that the temperature of the treated area is close to 2° C., it sends an instruction to the electronics 17 which informs the user that there is an imminent danger of a burn by activating a sound and/or light alarm device, for example such as a LED 18 (FIGS. 1, 2 and 3); all that is necessary when LED 18 flashes is to move the spray gun away slightly, to ensure that the temperature of the patient's skin does not drop below 0° C.; the treatment usually lasts between 30 and 50 seconds.

Cartridge 2 will have to be replaced or refilled when it is empty, in other words when it contains no more $CO_2$ in the liquid phase; it is known that at this moment, the cartridge 2 still contains carbon dioxide in gaseous form, which as mentioned above, is useless for cryotherapy; therefore it is very important to completely purge all residual gas inside cartridge 2 before it is completely removed from its support 3, which is fitted with a purge hole 19 (FIG. 4) for this purpose and which is used to purge residual gas in cartridge 2 while it is being unscrewed, and before it is completely separated from spray gun 1.

Obviously, the visual alarm 18 controlled by the infrared pyrometer 14 could be replaced or used in combination with any type of sound alarm that an expert in the subject would be able to adapt without any difficulty; similarly, it is obvious that for specific applications, it would be possible to use the control value output from the infrared pyrometer 14 when it detected that the temperature in the treatment area has reached 2° C., to automatically switch the electricity power supply to the device thus preventing dry ice from being sprayed; any other adaptation of the same type would naturally fall within the scope of the invention.

Figure 4:
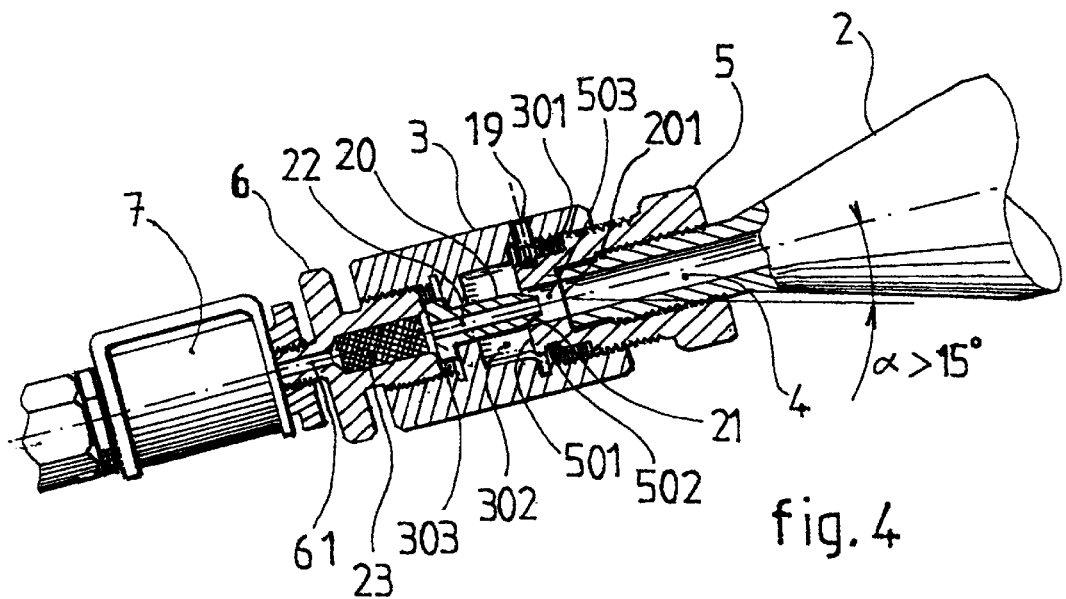
FIG. 4 is a partial view at a larger scale of the $CO_2$ cartridge drawing off head mounted on its support just before the cartridge sealing disk is struck.
Figure 5:
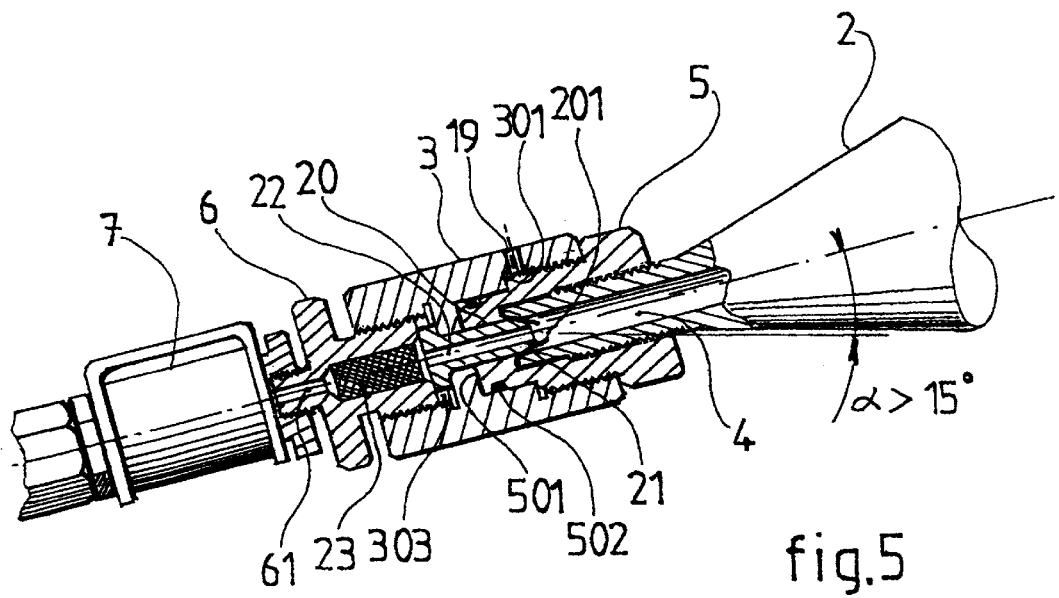
FIG. 5 is the same as the previous figure except that the cartridge is now completely engaged on its support after its sealing disk has been struck.

We will now describe the pressure reduction system for the liquid $CO_2$ inside the spray gun 1 in more detail, particularly with reference to FIGS. 1, 4 and 5.

The cartridge of $CO_2$, medicalized if necessary and liquefied under pressure, is actually a cartridge that conventionally comprises a cylindrical metal receptacle very similar to receptacles used in many types of equipment such as extinguishers, fitted with a drawing off head arranged to cooperate with a usage support. This cartridge may be designed for once only use or it may be refillable in other words it may be sold and refilled later by gas suppliers as is frequently done.

According to a preferred embodiment of the spray gun according to the invention, it would be equipped with single-use cartridges containing 160 g of $CO_2$, which is suitable for 40 to 50 seconds treatment and which avoids the need for users to have heavy equipment for refilling empty cylinders. With this particular embodiment, an innovative drawing off system was designed incorporating an automatic cartridge percussion system to limit risks during handling, in which the standard nut used on commercially available cartridges (for example like those sold by the French company VALLOUREC) is modified in order to maintain gas tightness during and after preparation of the bronze sealing disk 201 that closes the throwaway cartridge 2, as will be described later. Note that the thread used on nut 5 that screws onto the top of drawing off head 4 of cartridge 2, has been deliberately chosen among infrequently used threads so that it will be impossible to use cartridges on spray gun 1, unless they are specially designed for it.

The percussion system for cartridges 2 is composed of three parts as shown in FIGS. 4 and 5. A cylindrical support 3 comprising a first inlet chamber 301 threaded on the inside at the cartridge end, and nut 5 which is previously fitted onto the drawing off head 4 of cartridge 2 which is closed by a bronze sealing disk 201, is then screwed into the inlet chamber; a second chamber 302 in line with the first chamber 301 and smaller than this chamber, cooperates with the end 501 of nut 5, the diameter of which is smaller than the threaded part of the nut, in order to provide complete gas tightness, by means of an outside O-ring 502 fitted on the end 501 between cartridge 2 and the rest of the device as soon as the striker 20 perforates the bronze sealing disk 201. The striker 20 forming the second part of the system is composed of a fixed tip attached to support 3 that can engage in the hollow end part 503 of nut 5 surrounding the drawing off head 4 until coming into contact with sealing disk 201 when the nut 5 is sufficiently engaged into the support 3 to hold the assembly together rigidly; at this time, the tip 21 is in contact with the sealing disk 201 and the O-ring 202 is in contact with the walls of chamber 302 making a gas tight seal with the drawing off head 4; as shown in FIG. 5, the cartridge 2/nut 5 assembly then simply needs to be screwed further into support 3 to perforate the sealing disk 201, the $CO_2$ then being free to expand towards the lower part of support 3 passing firstly through a longitudinal duct 22 provided for this purpose along the center line of the striker 20 that opens up into a third coaxial chamber 303 in support 3 necessary for putting the percussion system 20 into position and supporting a filter 23 within the liquid $CO_2$ stream and designed to retain any machining residue, for example from cartridge 2. The filter 23 is covered by a nut 6 that cooperates with the internal thread of chamber 303 in a conventional manner. The nut 6, through which a duct 61 passes axially, is provided with a threaded pin on its downstream surface, used subsequently for installing the inlet of solenoid valve 7.

This solenoid valve, chosen from among existing high pressure solenoid valves, opens and closes an axial duct extending the previous duct 61 simply by electrically controlling an electromagnet placed on the center line of the solenoid valve. A frequently used assembly of an expansion tube 8 is fitted at the exit from solenoid valve 7, slightly curved to compensate for the inclination α of the cartridge on its support 3, thus connecting the drawing off head 4 without its sealing disk to the ejection point 9 from spray gun 1. Note that the $CO_2$ remains in liquid form until it reaches the outlet from solenoid valve 7 and no ice is formed that could prevent fluid circulation; the inside diameter of the pressure reduction tube 8 is made very small (of the order of 0.5 mm) in order to regulate the outlet flow of liquid $CO_2$. A PTFE tube is preferably used in order to prevent the formation of an ice plug at the outlet from the pressure reducer.

Considering the $CO_2$ pressure at the outlet from the cartridge 2 (which is of the order of 50 bars), the $CO_2$ flow rate inside the pressure reduction tube 8 is sufficiently large to force the dry ice outwards as microscopic particles that sublimate in the usage area or the area being treated.

The cartridge 2 will have to be replaced, or in another embodiment refilled, when it no longer contains any product in the liquid phase. In order to do this, the cartridge 2 should be removed from its support 3, which creates a problem of removing all residual gas inside the cartridge before the cartridge is taken off completely, in order to prevent a sudden recoil which could also be accompanied by a detonation. Therefore a purge hole 19 is provided between the outside and the chamber 301 placed on the inlet side of support 3 (in other words the chamber that does not include a percussion device 20) in order to purge the cartridge before it is withdrawn; this purge hole 19 (FIG. 4) purges the residual gas at the time that the cartridge 2 is removed by unscrewing nut 5 from its housing in chamber 301 in support 3; naturally, the inside geometry of this chamber 301 was designed so that, as soon as the head of cartridge 2 without the sealing disk moves away from the percussion tip 21, the residual gas is in contact with the purge hole 19, in other words with the outside, although the threaded length of the nut 5 still engaged in the chamber 301 is still sufficient to hold the assembly rigidly together and to prevent any sudden recoil of the cartridge released from its support; therefore the user should stop and wait until he cannot hear any gas escaping through purge hole 19, before continuing to unscrew nut 5 and remove cartridge 2 in order to replace it.

According to one particularly important characteristic of the invention, the spray gun 1 that has just been described above is used together with a device for checking the temperature of the application area to prevent the temperature drop which is beneficial for the treatment from causing any damage to the body tissues; consequently, according to a preferred embodiment of the invention, a second barrel 102 is fitted on the spray gun parallel to its barrel 101 containing the $CO_2$ pressure reduction system, the second barrel containing a temperature threshold detector 14 and its control electronics 17 capable of operating remotely without any contact with the application or treatment area, as shown in FIGS. 2 and 3 in the drawings. According to one preferred embodiment, in the special example of a spray gun designed for use in cryotherapy, an infrared pyrometer is chosen as a temperature threshold detector associated with the spray gun, preferably powered by a 12 volt DC power supply in the same way as solenoid valve 7; the optics of pyrometer 14 are arranged such that the field of vision corresponds as closely as possible to the target to be measured in the area of use or on the skin, in order to obtain an accurate and precise temperature readout. Consequently, the optics of pyrometer 14 are designed so that a 15 mm diameter target on the treatment area corresponds to a focusing spot on the detector with a diameter of about 1 mm, allowing for a distance between the pyrometer lens and the target of between 120 and 150 mm which, as described above, corresponds to optimum position of the apparatus with respect to the treatment area; if the treatment distance is too short, the temperature gradient in the skin could become so high that the difference between the temperature of the treated area and the temperature of the area scanned by the pyrometer is excessive, and the alarm set value would therefore be unreliable. On the other hand if the treatment distance is too long, the jet of dry ice and the infrared radiation would almost certainly overlap, with the result that the pyrometer would record the temperature of the jet, rather than the temperature of the treated area. Furthermore, the two barrels 101 and 102 are offset such that barrel 102 that contains the pyrometer 14 is setback from the other barrel to prevent any contamination of the optics by the sprayed $CO_2$.

The threshold detector in pyrometer 14 is set to a fixed temperature of +2° C., in order to maintain a safety margin from the critical temperature of 0° C. as mentioned above. This is done by coupling the pyrometer 14 to electronics 17 (FIG. 3) that also operates under a 12 volt DC power supply, for example as soon as the approach guide 13 is pulled completely outside the spray gun; it is thus possible to adjust the emissivity of the detector, which is defined as the ratio of the energy radiated by the treatment area on which the temperature is being measured, to the energy emitted by a black body at the same temperature. For example, it is known that the emissivity of skin, which is organic, is 0.95, and consequently pyrometer 14 will be preset to this value.

Similarly, it is obvious that the pyrometer must respond fairly quickly in order to check the temperature; at the same time the pyrometer response time must not be too short in order to clip extreme temperature values when doing the necessary forwards and backwards movements over the treated surface, as described above. Under these conditions, the response time will be preset to about 5 seconds.

When the threshold of +2° C. is reached, in other words as soon as the temperature of the area to be treated drops below the value of 2° C, the electronics 17 triggers a sound and/or a visual alarm such as a LED 18 in order to warn the user either to stop spraying or temporarily remove spray gun 1 from the treatment area. Naturally, it is obvious that many alternate embodiments could be considered, for example automatically cutting spraying off by switching off the power supply to solenoid valve 7 as soon as the temperature threshold is reached.

It is obvious that the characteristics of the infrared pyrometer 14 described above are only one preferred example of an embodiment of the invention, and that many other settings satisfying particular or specific needs could also be envisaged without going outside the scope of the invention; similarly, other remote temperature detectors could be used without changing the essential characteristics of the invention. Finally, it would be possible to envisage replacing pressurized carbon dioxide by other liquefied gases, for example argon; at the present time, although practically identical results can be obtained using other gases, carbon dioxide is by far the most suitable gas for a portable and self-contained cryotherapy apparatus to be used for the treatment of man or animals, or other cryogenic applications outside the medical field.

What is claimed is:

1. In a self-contained cryogenic apparatus that operates at a temperature on the order of −78° C. at atmospheric pressure reached by reducing the pressure of carbon dioxide ($CO_2$) in liquid/solid phase, comprising a reservoir of pressurized liquefied $CO_2$; a drawing off head connected to a liquid/solid $CO_2$ pressure reduction and ejection system, and comprising a control device, a pressure reduction device and a means for checking the temperature in the area to which the $CO_2$ is applied, the improvement wherein the top of the $CO_2$ reservoir is arranged on the apparatus such that during an entire period of usage, only the liquid part of the $CO_2$ inside the reservoir comes into contact with the head so that the liquid part of $CO_2$ is drawn off and forced towards the application area through the pressure reduction and ejection system.

2. The apparatus according to claim 1, wherein the reservoir is in the general shape of a compressed gas cartridge fitted with the drawing off head at its end; the apparatus further comprising means for attachment to and detachment from the apparatus, and devices for setting up a communication towards the pressure reduction and ejection system; said reservoir during the usage period being located at a higher level than the apparatus, such that the center line of the cartridge is inclined in the vertical plane and the drawing off head faces downwards towards the apparatus to which it is fixed.

3. The apparatus according to claim 2, wherein the means for attachment are arranged such that the center line of the cartridge is inclined from the horizontal plane by at least 15° during the usage period.

4. The apparatus according to claim 1, wherein the drawing off head fitted on a cartridge, which is comprised of a cylindrical end piece threaded on the outside and closed by a sealing disk, is attached to a cartridge support in the apparatus through a part that fastens said drawing off head when the cartridge is screwed into the support firstly to bring the sealing disk into contact with a percussion device fixed in an appropriate position along the center line of the support, and then to perforate said sealing disk while maintaining the gas tightness of the assembly, in order to draw off $CO_2$ in the liquid phase through an axial duct passing through from one side of the percussion device to the other; the free end of the duct being connected to the pressure reduction and ejection system; a purge hole between the inside of the support and the outside being provided radially in a part of the support that does not include the percussion device for purging a residual $CO_2$ gas from the empty cartridge while unscrewing and before complete separation from the apparatus.

5. The apparatus according to claim 4, further comprising a solenoid valve operating in "On-Off" for creating the communication between the outlet from the percussion device and the pressure reduction system.

6. The apparatus according to claim 1, wherein the pressure reduction and ejection system comprises a tubing having a small inner diameter for achieving a sufficiently high $CO_2$ flow rate to eliminate microscopic particles of dry ice which sublimate in the application area.

7. The apparatus according to claim 2, and having the general shape of a spray gun, which comprises at least one casing that contains a barrel and a handle fitted with a main control trigger behind the $CO_2$ cartridge; the ergonomy of the control trigger being such that when a user holds the spray gun in his hand normally, the barrel is approximately horizontal, automatically keeping the cartridge inclined at an angle α downwards.

8. The apparatus according to claim 7, wherein the barrel contains a cartridge support opening up towards the back and all devices in the pressure reduction system leading to the liquid $CO_2$ ejection system at the front; control power supply devices and an ejection control switch being housed inside the handle; and a temperature detector for detecting the temperature in the application area being attached parallel to the barrel, accurately offset backwards from an ejection point to prevent any interaction between operation of the detector and flow of sprayed $CO_2$.

9. The apparatus according to claim 8, wherein the temperature detector is not in contact with the application area.

10. The apparatus according to claim 9, wherein the temperature detector is an infrared pyrometer.

11. The apparatus according to claim 10, wherein the focal distance of the infrared pyrometer is such that there is no interaction between sprayed dry ice and the temperature is measured precisely when the apparatus is positioned at a suitable distance for the planned usage.

12. The apparatus according to claim 11, wherein the suitable distance between the apparatus and the application area is given by an approach guide.

13. The apparatus according to claim 12, wherein the approach guide comprises a rod parallel to and under the barrel of the spray gun and sliding from a rest position inside the barrel to a working position outside the barrel corresponding to a suitable distance for optimum spraying of dry ice.

14. The apparatus according to claim 13, wherein the rod which is fitted with at least one bossing that acts as an extension stop when it moves, cooperates with an electric switch which is closed by said bossing to enable the apparatus to be switched on.

15. The apparatus according to claim 10, wherein the infrared pyrometer is coupled to one of a visual alarm and a sound alarm for automatically switching off the apparatus electric power supply when the temperature drop in the application area reaches a 2° C. threshold.

16. The apparatus according to claim 10, wherein for a target diameter approximately equal to 15 mm in the application area, the pyrometer is preset to an emissivity ratio of 0.95 at a response time of 5 seconds, and the optics are selected to give a focal distance of between 120 and 150 mm.

17. Method for the treatment of a human or animal patient which comprises spraying dry ice onto the patient's skin using the self-contained and portable cryotherapy apparatus of claim 1.

* * * * *